(12) United States Patent
Meng et al.

(10) Patent No.: US 10,338,354 B2
(45) Date of Patent: Jul. 2, 2019

(54) ACHROMATIC ANASTIGMATIC ANAMORPHIC OBJECTIVE

(71) Applicant: Coherent, Inc., Santa Clara, CA (US)

(72) Inventors: Lei Meng, Wilsonville, OR (US); Michele Wayne Winz, Woodburn, OR (US)

(73) Assignee: COHERENT, INC., Santa Clara, CA (US)

( * ) Notice: Subject to any disclaimer, the term of this patent is extended or adjusted under 35 U.S.C. 154(b) by 0 days.

(21) Appl. No.: 15/646,688

(22) Filed: Jul. 11, 2017

(65) Prior Publication Data
US 2018/0017769 A1    Jan. 18, 2018

Related U.S. Application Data

(60) Provisional application No. 62/363,532, filed on Jul. 18, 2016.

(51) Int. Cl.
G02B 13/18    (2006.01)
G02B 13/08    (2006.01)
(Continued)

(52) U.S. Cl.
CPC .......... G02B 13/08 (2013.01); G01N 15/1434 (2013.01); G02B 9/16 (2013.01);
(Continued)

(58) Field of Classification Search
CPC ...... G02B 13/08; G02B 13/0035; G02B 9/16; G02B 27/0905; G02B 27/0911;
(Continued)

(56) References Cited

U.S. PATENT DOCUMENTS 4,963,900 A * 10/1990 Budd ................ H04N 1/1135
                                                    347/137
5,185,758 A *  2/1993 Fan .................. H01S 3/09415
                                                    372/101
(Continued)

FOREIGN PATENT DOCUMENTS

DE     102013225310 B3    5/2015
JP        60-229007 A    11/1985
(Continued)

OTHER PUBLICATIONS

International Search Report and Written Opinion received for PCT Patent Application No. PCT/US2017/042007, dated Dec. 1, 2017, 17 pages.
(Continued)

*Primary Examiner* — William R Alexander
(74) *Attorney, Agent, or Firm* — Morrison & Foerster LLP

(57) ABSTRACT

In a flow cytometer, an objective lens for focusing an input laser-radiation beam including at least four different laser-radiation wavelengths in a common plane includes only three singlet lens-elements. Two of the elements are cylindrical elements arranged as a cylindrical telescope for shaping and reducing the size of the input laser-beam. The third element is a spherical element arranged to focus the reduced size beam in the common plane. In one example, all three elements are made from the same optical material.

7 Claims, 7 Drawing Sheets

(51) Int. Cl.
  *G01N 15/14* (2006.01)
  *G02B 9/16* (2006.01)
  *G02B 27/09* (2006.01)
  *G02B 27/10* (2006.01)
  *G02B 27/14* (2006.01)
  *G02B 13/00* (2006.01)
  *A61B 5/00* (2006.01)

(52) U.S. Cl.
  CPC ..... *G02B 13/0035* (2013.01); *G02B 27/0905* (2013.01); *G02B 27/0911* (2013.01); *G02B 27/0966* (2013.01); *G02B 27/1006* (2013.01); *G02B 27/145* (2013.01); *A61B 5/0071* (2013.01); *G01N 2015/1438* (2013.01); *G01N 2015/1452* (2013.01)

(58) Field of Classification Search
  CPC ............ G02B 27/0966; G02B 27/1006; G02B 27/145; G01N 15/1434; A61B 18/201
  USPC ......................................................... 359/634
  See application file for complete search history.

(56) References Cited

U.S. PATENT DOCUMENTS

| | | | | |
|---|---|---|---|---|
| 5,761,234 A | * | 6/1998 | Craig | H01S 3/094003 |
| | | | | 372/33 |
| 5,764,677 A | * | 6/1998 | Scheps | H01S 3/094034 |
| | | | | 372/20 |
| 6,356,574 B1 | * | 3/2002 | Craig | H01S 3/094003 |
| | | | | 372/50.1 |
| 7,787,197 B2 | | 8/2010 | Chen | |
| 2003/0058440 A1 | * | 3/2003 | Scott | G01J 3/10 |
| | | | | 356/318 |
| 2013/0003343 A1 | * | 1/2013 | Sudarshanam | G02B 27/48 |
| | | | | 362/19 |
| 2014/0036943 A1 | * | 2/2014 | Janssens | H01S 3/10061 |
| | | | | 372/27 |
| 2016/0322777 A1 | * | 11/2016 | Zediker | H01S 5/4012 |
| 2017/0227763 A1 | * | 8/2017 | Uragami | G02B 27/0101 |
| 2017/0271837 A1 | * | 9/2017 | Hemenway | G02B 6/03638 |

FOREIGN PATENT DOCUMENTS

| | | |
|---|---|---|
| WO | 2001/078633 A2 | 10/2001 |
| WO | 2001/078633 A3 | 7/2002 |
| WO | 2011/109763 A2 | 9/2011 |
| WO | 2011/109763 A3 | 3/2012 |

OTHER PUBLICATIONS

Invitation to Pay Additional Fees received for PCT Patent Application No. PCT/US2017/042007, dated Sep. 29, 2017, 5 pages.

* cited by examiner

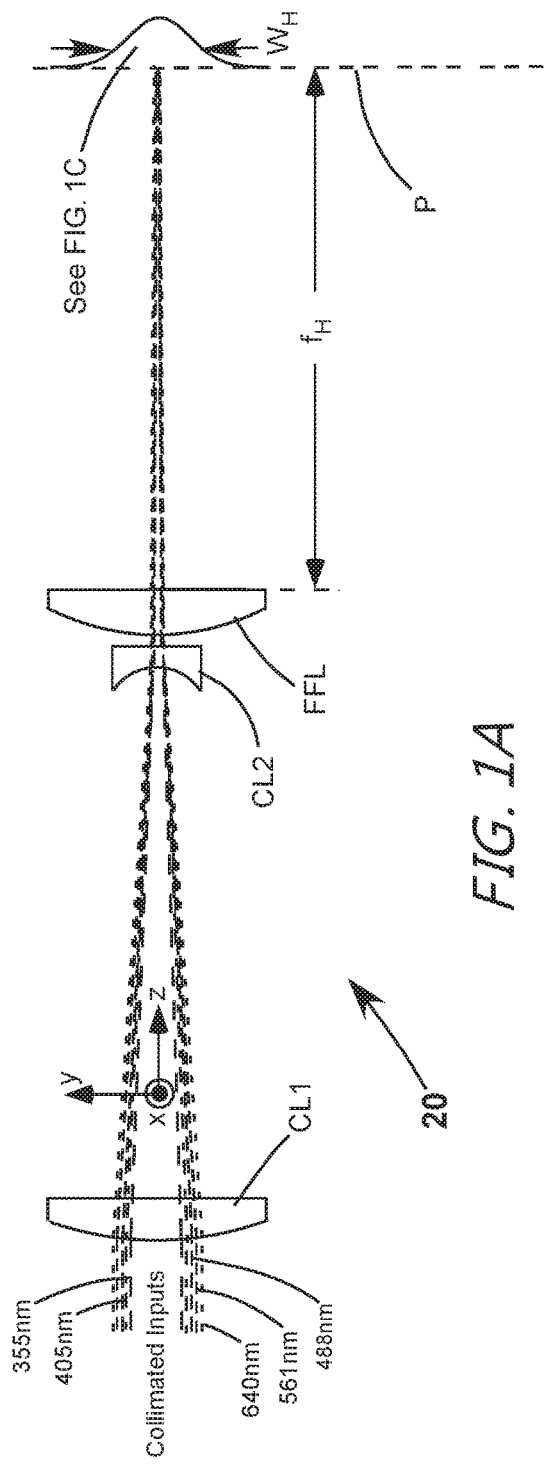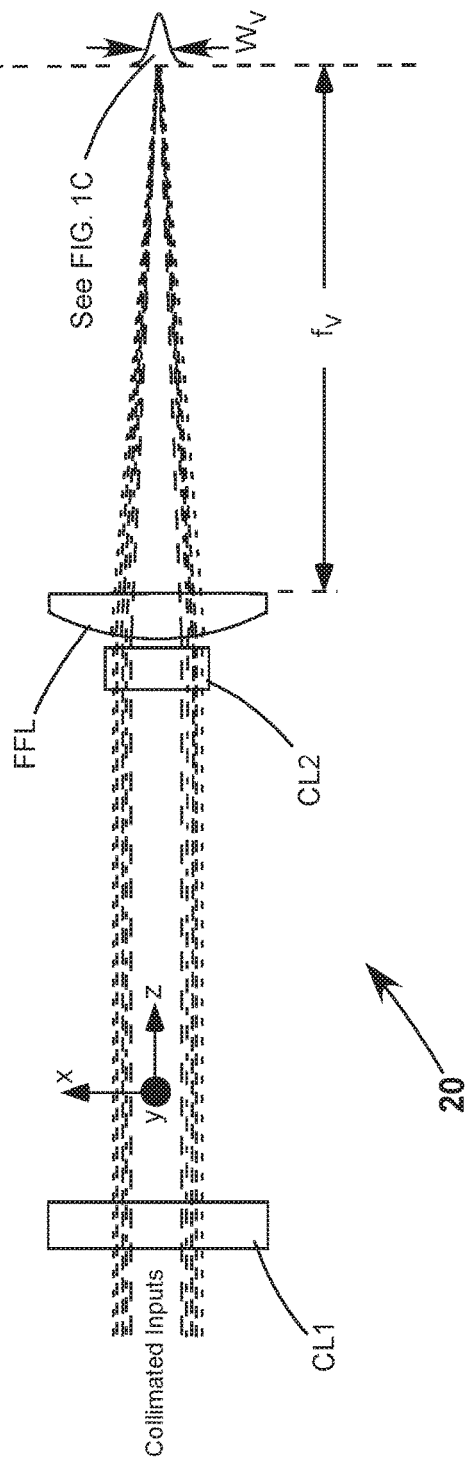

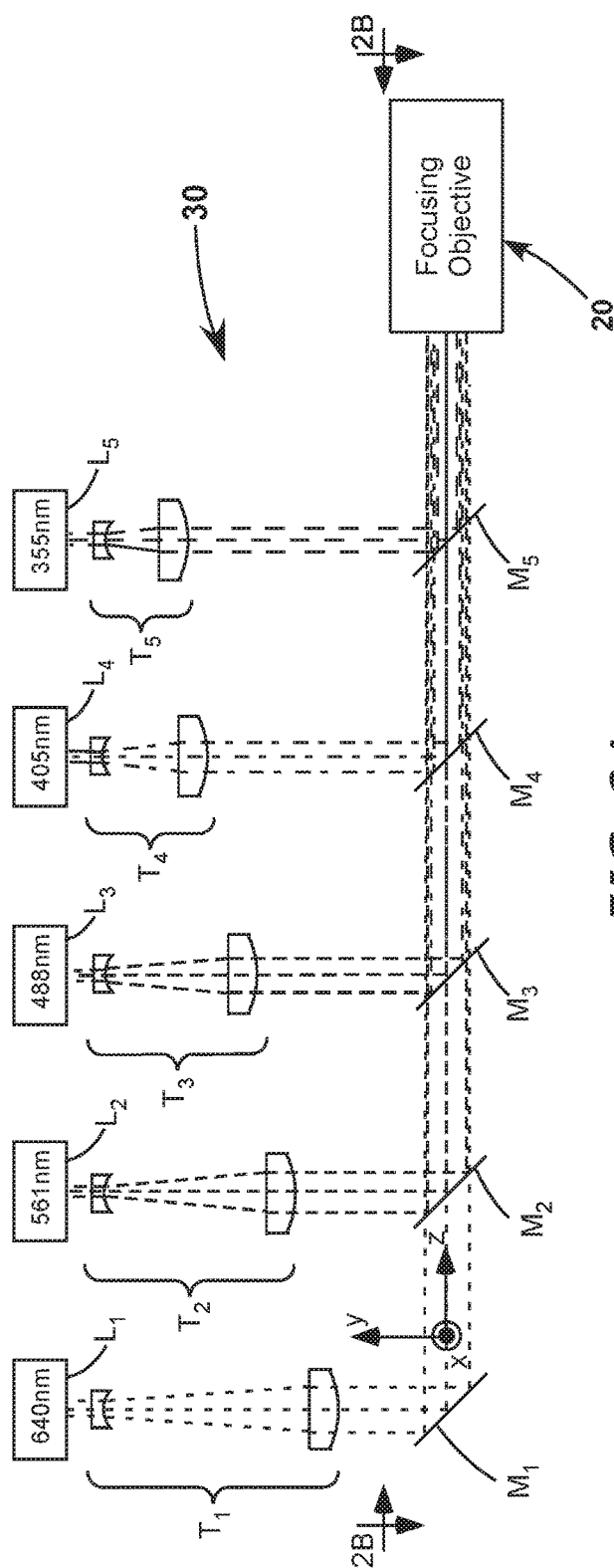
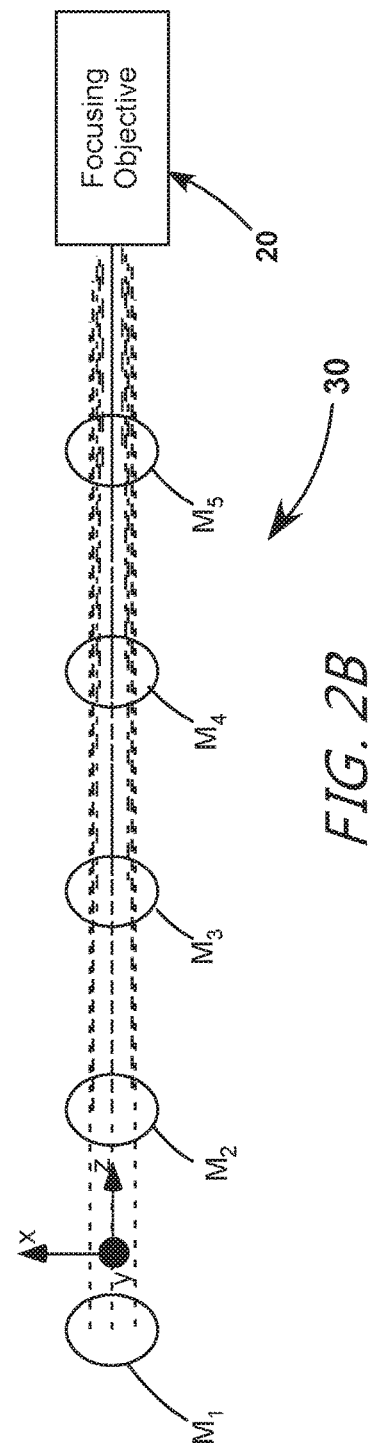
FIG. 2A
FIG. 2B

US 10,338,354 B2

ACHROMATIC ANASTIGMATIC ANAMORPHIC OBJECTIVE

PRIORITY

This application claims priority to U.S. Provisional Application Ser. No. 62/363,532, filed Jul. 18, 2016, the disclosure of which is incorporated herein by reference in its entirety.

TECHNICAL FIELD OF THE INVENTION

The present invention relates in general to projection lenses. The invention relates in particular to anamorphic projection lenses for focusing two or more laser-beams having different wavelengths into a common elliptical focal-spot.

DISCUSSION OF BACKGROUND ART

A basic principle of flow cytometry is the passage of cells in a fluid-stream through a focused laser-beam so that the cells can be detected, identified, counted, and sorted. Cell components are fluorescently labelled and then excited by the laser-beam to emit light at varying wavelengths. The fluorescence can then be measured to determine the amount and type of cells present in a sample. Up to thousands of particles per second can be analyzed as they pass through the fluid-stream.

Several detectors are carefully placed around the fluid-stream at the point where the fluid passes through the focused beam. The suspended particles or cells, which may range in size from 0.2 micrometers (µm) to 150 µm, pass through the focused beam and scatter the radiation. The fluorescently labelled cell components are also excited by the focused laser-beam and emit light (fluorescence) at a longer wavelength than that of the laser-beam. The fluorescence is then detected by the detectors. The detectors measure a combination of scattered and fluorescent light. Measurement data is then analyzed, using special software, by a computer that is attached to the flow cytometer.

It is generally accepted that the above described flow cytometry process is more flexible and more accurate the more light-wavelengths that are included in the laser-beam. In practice, this is accomplished by combining component beams from different lasers along a common path to provide a combined beam that is focused into the fluid-stream. Diode-laser modules are typically used for providing the component beams. Commercially available diode-laser modules can provide laser radiation at selected fundamental wavelengths in a range from the near ultraviolet (UV) the near infrared (NIR).

An increasing number and range of wavelengths presents significant problems in the design and construction of an optical objective for focusing the combined laser-beam into the fluid-stream. It is generally accepted that for focusing two significantly different wavelengths at a common location (focal plane) a focusing objective must include at least two lens elements having different, for example high and low, spectral dispersion. An objective arranged to focus two different wavelengths (red and blue) in a common focal plane is generally referred to as an achromatic objective.

If three significantly different wavelengths, for example, red, green, and blue wavelengths, are to be focused at a common location, a focusing objective must include at least three lens elements having different spectral dispersion. An objective arranged to focus three significantly different wavelengths (red, green, and blue) in a common focal plane is generally referred to as an apochromatic objective.

In either achromatic or apochromatic objectives individual (singlet) lens elements of different spectral dispersion may need to be "cemented" together in a form referred to by practitioners of the lens design art as "doublets" or "triplets". This could provide a problem in including UV wavelengths in a flow cytometer, as optical cements (adhesives) may be degraded by the UV radiation Based on conventional optical design wisdom, it can be expected that as more laser-radiation wavelengths, for example four or more, are included in a flow cytometer, the more complex and expensive will be the objective required to focus the wavelengths into the fluid-stream. This could result in the cost and complexity of a focusing objective determining a practical upper limit to how many laser-radiation wavelengths could be used in a flow-cytometer.

There is need for a simple focusing objective, capable of focusing four or more laser radiation wavelengths in a common focal plane, but wherein the number of different optical materials (glasses) required is less than the number of different wavelengths to be focused by the objective in the common focal plane. Preferably the focusing objective should not include any cemented doublet or triplet elements.

SUMMARY OF THE INVENTION

In one aspect of the present invention, an objective lens for focusing an input beam of laser-radiation in a focal plane, comprises first, second, and third optical elements in consecutive numerical order in a propagation direction of the beam. The first optical element is a cylindrical element having a focal length $f_{CL1}$. The second optical element is a cylindrical element having a focal length $f_{CL2}$. The third optical element is a spherical element having a focal length $f_{FFL}$. The focal lengths $f_{CL1}$, $f_{CL2}$, and $f_{FFL}$ are related by an equation $f_{CL1} - f_{CL2} = G \cdot f_{FFL}$, where G is between about 0.7 and about 1.4, and preferably between about 0.9 and about 1.1.

In another aspect of the present invention, optical apparatus comprises at least first, second, third, and fourth lasers delivering respectively first, second, third, and fourth component laser-beams at respectively first, second, third, and fourth wavelengths. A beam combiner is arranged to combine the first, second, third, and fourth component laser-beams into a combined beam. An objective lens is provided including only three singlet optical elements. The objective lens is arranged to receive the combined laser-beam and focus the combined laser-beam such that the component laser-beams thereof are all focused about in a common focal plane.

The terminology "about in a common focal plane" recognizes that laser-beams, when focused, are focused into smallest diameter (focal spot) of what is termed a "beam waist" by practitioners of the art. The beam converges on one side of the focal spot and diverges on an opposite side of the focal spot. The waist is further characterized by a "Raleigh range" which is the distance from the focal spot to a point where the beam diameter is equal to $\sqrt{2}$ times the smallest diameter. "About in a common focal plane", in this description and the appended claims, means that the focal spots of the component beams are within a Rayleigh range of that common focal plane.

BRIEF DESCRIPTION OF THE DRAWINGS

FIG. 1A and FIG. 1B are respectively horizontal and vertical views of one preferred embodiment of a three-element anamorphic focusing objective in accordance with the present invention in including a positive cylindrical lens element, a negative cylindrical lens element, and a spherical lens element listed in the direction of propagation of radiation through the lens, with five input beams being focused, each beam having a different wavelength from any other.

FIG. 2A and FIG. 2B are respectively horizontal and vertical views of one preferred example of a beam-combiner, combining the outputs from five laser-radiation sources into a collinear bundle of beams for focusing by the objective of FIGS. 1A and 1B.

DETAILED DESCRIPTION OF THE INVENTION

Figure 1C:
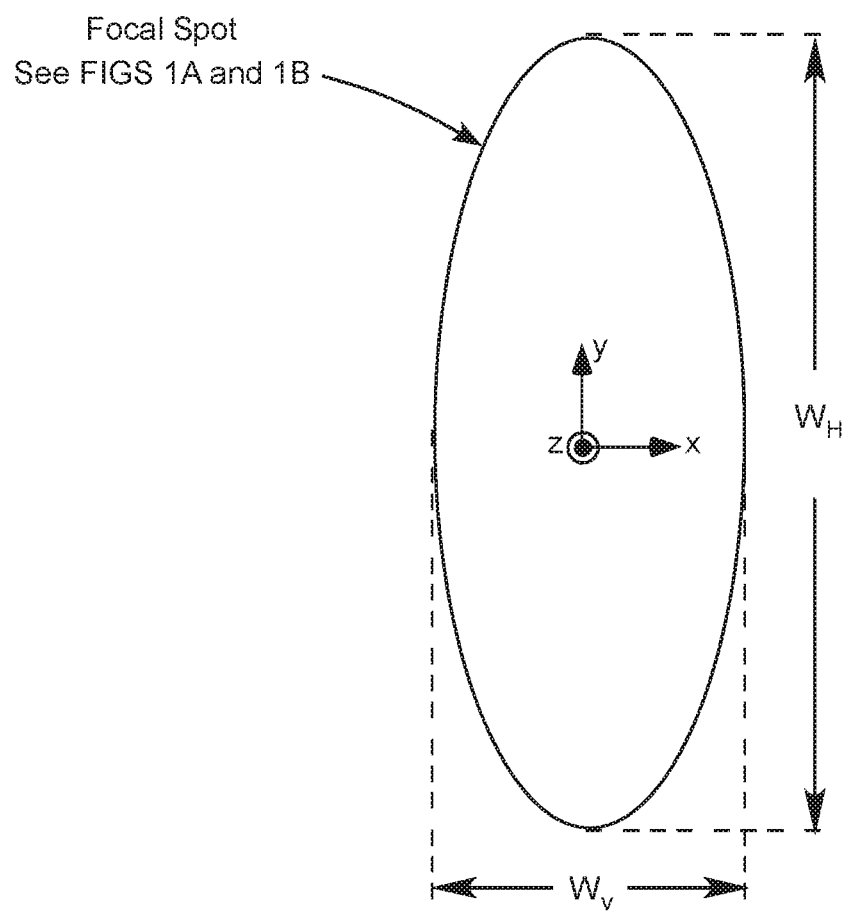
FIG. 1C is a view perpendicular to the views of FIG. 1A and FIG. 1B, schematically illustrating details an elliptical focal-spot produced by the objective of FIGS. 1A and 1B from the input beams.

Turning now to the drawings, FIGS. 1A and 1B schematically illustrate a preferred embodiment 20 of an achromatic anastigmatic anamorphic focusing objective in accordance with the present invention. FIG. 1A is a view designated arbitrarily as a "horizontal" view. This is a view in a y-z plane defined by arbitrarily assigned Cartesian optical axes x, y, and z, where z is the propagation-axis (propagation direction) of light through the lens. FIG. 1B is a view designated arbitrarily as a vertical view, i.e., perpendicular to the view of FIG. 1A, i.e., a view in an x-z plane defined by the Cartesian optical axes.

Objective 20 includes cylindrical lens elements CL1 and CL2, having optical power in only the y-axis. Elements CL1 and CL2 are followed in the propagation-axis by final focusing element FFL. Element FFL has equal optical power in both the x-axis and the y-axis and be referred to generally as a rotationally symmetrical element. A spherical optical element is preferred for production cost considerations.

In this embodiment, element CLI has positive optical power in the y-axis (horizontal plane), and element CL2 has negative optical power in the y-axis. The elements preferably have a plane surface and a curved surface as depicted in the drawing and are preferably arranged with such that radiation is incident first on the curved surface of each element in the direction of propagation. i.e., in the z-direction.

Objective 20 is configured to bring nominally collimated, collinear beams of different wavelengths to a focus in a working plane P. Here the wavelengths, for purposes of this description, are 640 nanometers (nm), 561 nm, 488 nm, 405 nm, and 355 nm. The invention, however, is applicable to other wavelengths in the same or a different range. Ideally, the horizontal focus (working distance $f_H$ from the FFL) and the vertical focus (working distance $f_v$ from the FFL) should ideally be exactly the same, for all of the input wavelengths. This is not achievable in practice, but can be closely approximated as described further herein below. The diameters of the input beams are preferably about linearly related to the beam-wavelength as indicated in the drawing As summarized above, focal lengths $f_{CL1}$, $f_{CL2}$, and $f_{FFL}$ are related by an equation $f_{CL1} - f_{CL2} = G \times f_{FFL}$, where, $f_{CL1}$, $f_{CL2}$, $f_{FFL}$ are the focal lengths of elements CL1, CL2, and FFL, respectively, and G is between about 0.7 and about 1.4, and preferably between about 0.9 and about 1.1. Efforts to analytically determine the factor G in the equation $f_{CL1} - f_{CL2} = G * f_{FFL}$ were unsuccessful. Values of G between about 0.7 and 1.4 and between about 0.9 and 1.1 were determined empirically, and used to define a set of initial optical designs which could be readily optimized to provide a practical, functional optical design. Such optimization can be carried out using commercially available ray-tracing software. In examples described herein, optimizations were carried out using ZEMAX available from Zemax, LLC, of Kirkland, Wash.

Continuing with reference to FIGS. 1A and 1B, objective 20 is designed to focus input wavelengths into an elliptical focal spot having a width (major-axis) $W_H$ in the horizontal (y-z) plane, and a width (minor-axis) $W_V$ in the vertical (x-z) plane, as depicted in FIG. 1C. The ratio $W_H:W_V$ is determined primarily by the ratio of the focal lengths of elements CL1 and CL2. In an above-described flow cytometer, the minor-axis would be aligned with the flow-direction.

FIGS. 2A and 2B are respectively horizontal-plane and vertical-plane views schematically illustrating a preferred arrangement for combining beams of different wavelengths for input into inventive objective 20. Lasers $L_1$, $L_2$, $L_3$, $L_4$, and $L_5$ provide radiation at respectively the 640 nm, 561 nm, 488 nm, 405 nm, and 355 nm wavelengths. Afocal beam-expanding telescopes $T_1$, $T_2$, $T_3$, $T_4$, and $T_5$ are associated with lasers $L_1$, $L_2$, $L_3$, $L_4$, and $L_5$ respectively for forming the beams into required sizes relative to the laser wavelength and to collimate the beams. Here again, the near-linear relationship of beam diameter to wavelength is evident. Each telescope, in turn, can be adjusted to adjust the collimation of the expanded laser-beams. Mirror $M_1$, and dichroic mirrors $M_2$, $M_3$, $M_4$, and $M_5$ are arranged as a beam-combiner to combine the beams into a collinear bundle for input into objective 20. Note that FIG. 2B is seen in the direction 2B-2B of FIG. 2A and depicts only the mirrors forming the beam combiner, and the objective lens.

Figure 3:
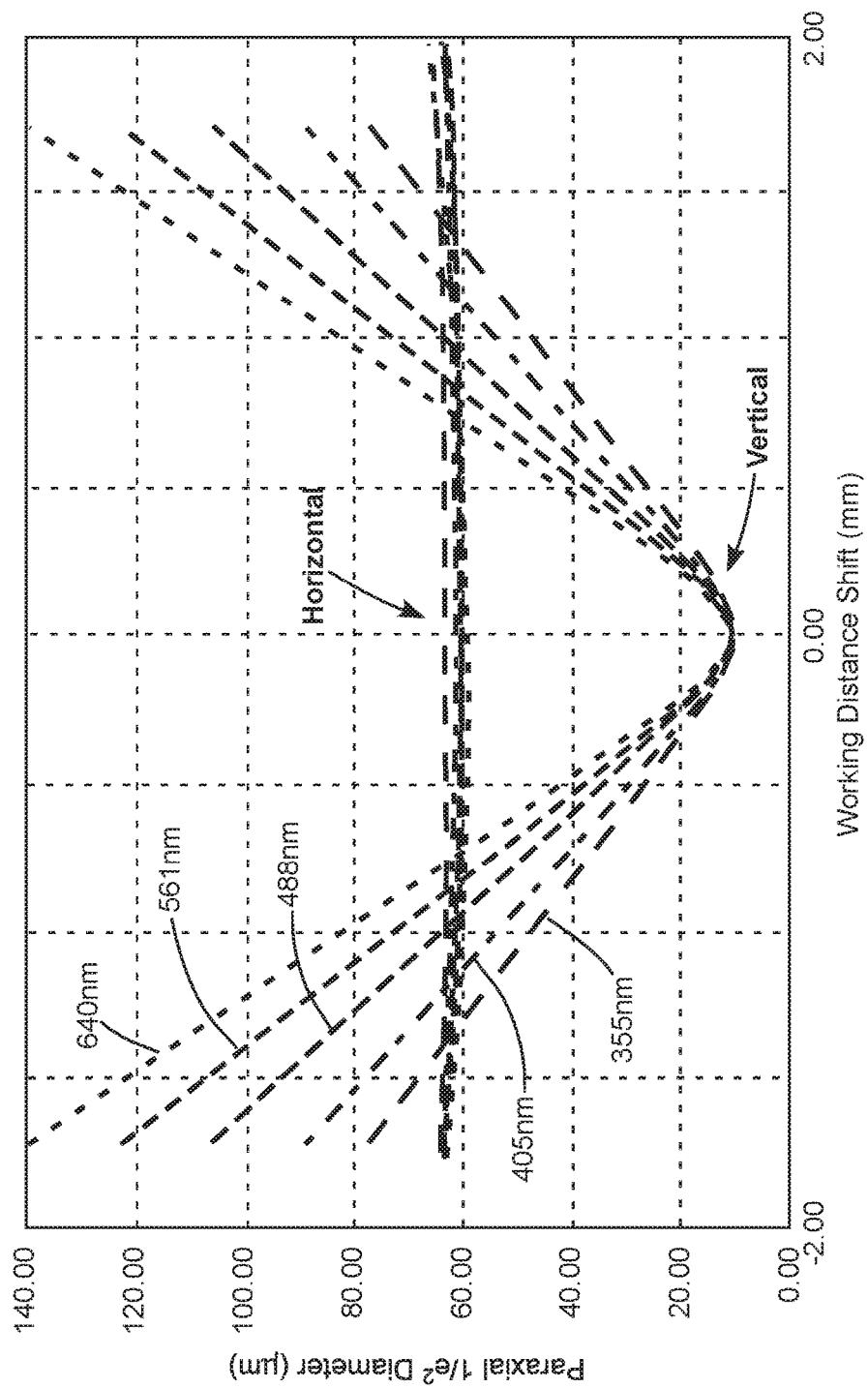
FIG. 3 is a graph schematically illustrating calculated paraxial $1/e^2$ beam-diameter as a function of working distance shift for one example of the objective of FIGS. 1A and 1B focusing 640 nm, 561 nm, 488 nm, 405 nm, and 355 nm collimated beams from the beam combiner of FIGS. 2A and 2B into an elliptical focal spot with a 6:1 axis ratio.

FIG. 3 is a graph schematically illustrating calculated paraxial $1/e^2$ beam-diameter as a function of working distance shift for an example of objective 20 focusing 640 nm, 561 nm, 488 nm, 405 nm, and 355 nm collimated beams from combiner 30 of FIGS. 2A and 2B. The term "working distance shift" is the difference between the calculated beam-waist position and the position of working plane P of FIGS. 1A and 1B.

Specifications of this example of objective 20 are listed in Table 1 below. EFL is the effective focal length of a lens element. Elements CL1 and CL2 have an EFL in the y-axis only. All lens elements are assumed to be made from fused silica.

TABLE 1

| Lens | EFL (mm) | Center Thickness (mm) | Distance to Previous Lens (mm) |
|---|---|---|---|
| CL1 | 42.3 | 4 | N/A |
| CL2 | −7.05 | 2 | 32.5 |
| FFL | 50 | 4 | 1 |

The EFLs of elements CL1 and CL2 are selected to provide an elliptical focal spot with a 6:1 ratio of major to minor axes. The beam-waist positions in the vertical plane for all wavelengths are coincident, by design, in the working plane. In the horizontal plane, the working distance shifts for the 355 nm, 405 nm, 488 nm, 561 nm, and 640 nm beams are 0.23 mm, −0.19 mm, −0.19 mm, −0.3 mm, and 0.16 mm, respectively. These shifts are relatively small compared with the Rayleigh range of the horizontal beam-waists, which is about 10.0 mm for this 6:1 ratio example, and, accordingly, not visible on the graph. Because of this, objective 20 can be realistically considered as astigmatic.

The height of the vertical beam waists at locations beyond the focus provides an indication of input beam sizes at different wavelengths. By way of example it can be seen that at a distance of −1.5 mm from the focus, the vertical beam waist diameters for 640 and 355 mm are about 120 micrometers (μm) and 68 μm respectively, with ratio of the wavelengths and beam diameters being the same at about 1.8. It is emphasized here that for any given ratio of horizontal-to-vertical ratio of focal spot-size, independent of the focal length of lens element FFL, there is only one optimum value of the focal length of lens element CL1, for which an equation $f_{CL1}-f_{CL2} \approx F_{FFL}$ is satisfied.

Figure 4:
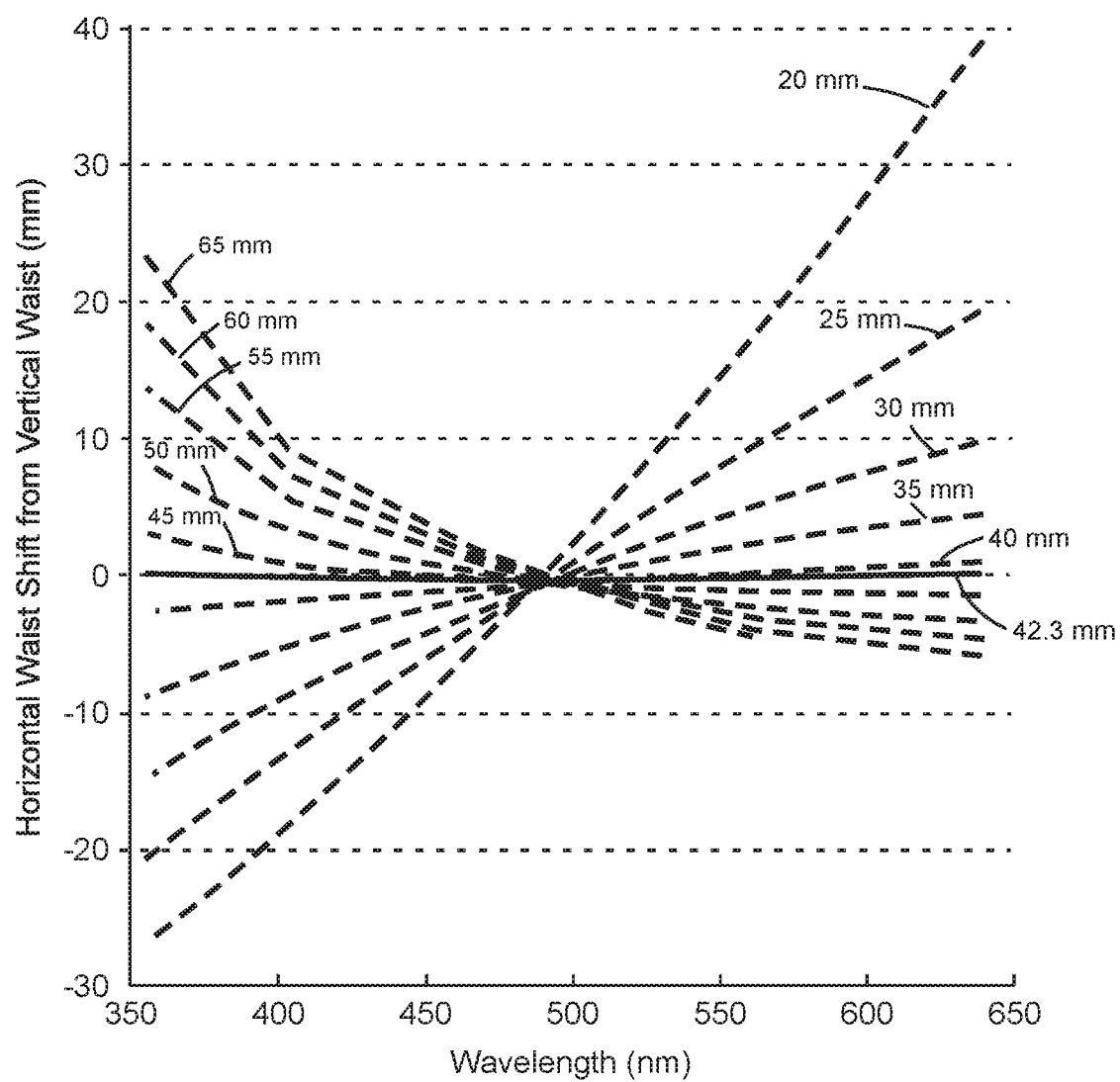
FIG. 4 is a graph schematically illustrating calculated horizontal waist shift from vertical focus as a function of wavelength for various values of the focal length of positive cylindrical lens element of FIGS. 1A and 1B.

By way of demonstration, FIG. 4 is a graph schematically illustrating calculated horizontal waist shift from vertical focus as a function of wavelength for various values of $f_{CL1}$ for a 6:1 spot-size ratio and $f_{FFL}$ of 50 mm. All lenses elements are assumed to be made from fused silica.

It can be seen that a value for $f_{CL1}$ of 42.3 mm provides that horizontal and vertical foci are essentially coincident in the range of wavelengths from 350 nm to 650 nm. The focal length of CL2 ($f_{CL2}$) for providing a spot-size ratio of exactly 6:1 is 7.05 mm (negative) which provides for $f_{CL1}-f_{CL2}=49.35$ mm, i.e., $0.987*f_{FFL}$.

Given that some shifts are relatively small compared with the Rayleigh range of the horizontal beam-waists, as discussed above with reference to the graph of FIG. 3, other values of $f_{CL1}$ can provide an acceptable, if not necessarily optimum result. By way of example, an acceptable result may be obtained with $f_{CL1}$, having any value between about 30 mm and about 50 mm. It is this consideration that was used to empirically establish preferred values of the factor G in the equation $f_{CL1}-f_{CL2}=G*F_{FFL}$ discussed above.

In discussions presented above, a spot-size ratio (horizontal to vertical) of 6:1 is assumed. The inventive focusing objective is not limited, however, to that particular ratio. Exemplary specifications for other ratios are provided in TABLE 2, still, of course, with only the three singlet lens elements CL1, CL2, and FFL.

TABLE 2

| Ratio of EFL CL1:CL2 | Optimum EFL of CL1 (mm) | Optimum EFL of CL2 (mm) | EFL of FFL (mm) |
|---|---|---|---|
| 2:1 | 31.69 | −15.85 | 50 |
| 4:1 | 39.03 | −9.78 | 50 |
| 6:1 | 42.3 | −7.05 | 50 |
| 8:1 | 44.45 | −5.56 | 50 |
| 10:1 | 46.69 | −4.66 | 50 |

The lens element material of each specification is assumed to be fused silica. It should be noted that the focal lengths of the cylindrical lens elements is referenced at a wavelength of 488 nm, while the focal length of element FFL, here assumed to be an "off the shelf" available element is referenced at a wavelength of 587.6 nm.

Figure 5:
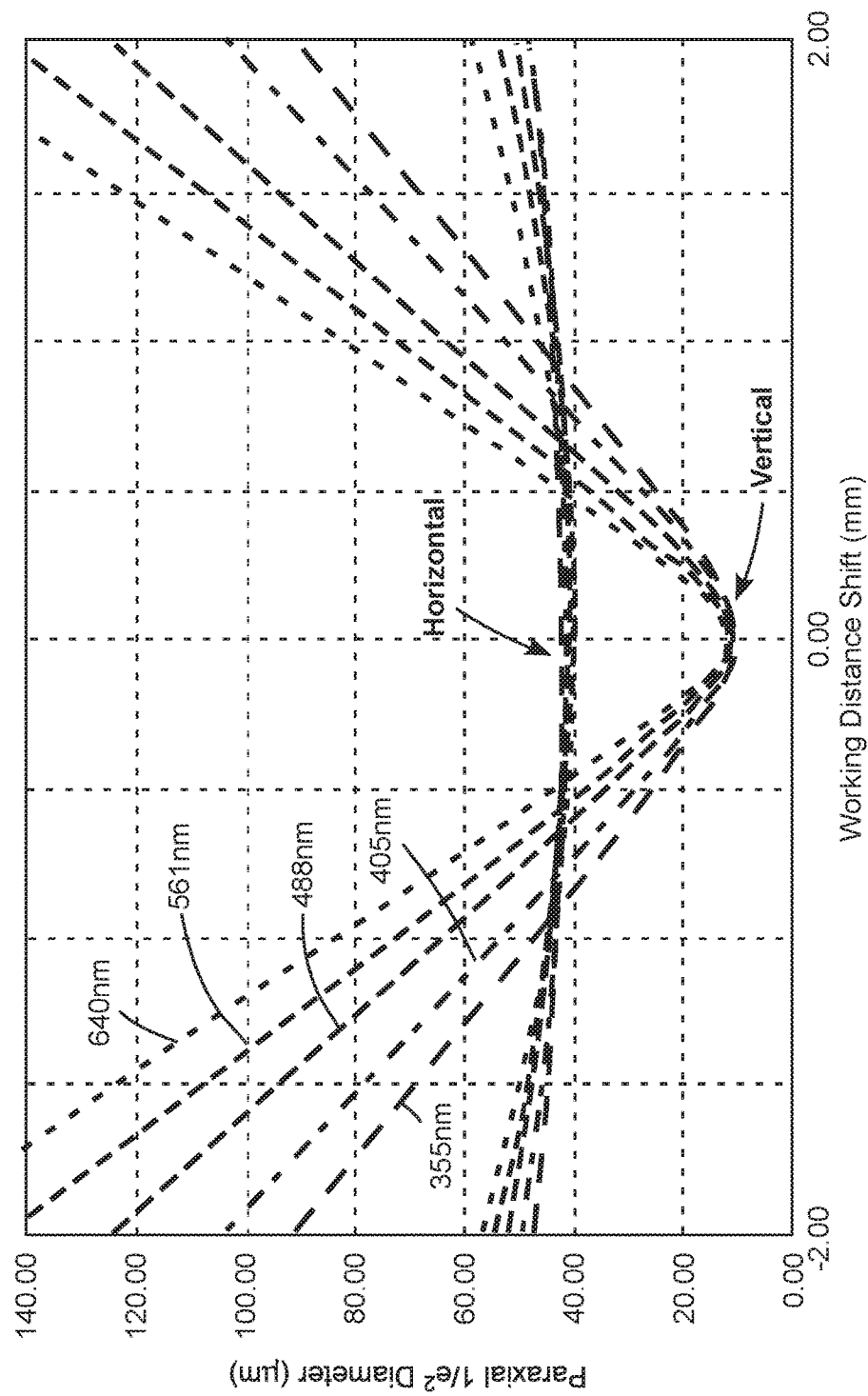
FIG. 5 is a graph schematically illustrating calculated paraxial $1/e^2$ beam-diameter as a function of working distance shift for another example of the objective of FIGS. 1A and 1B focusing 640 nm, 561 nm, 488 nm, 405 nm, and 355 nm collimated beams from the beam combiner of FIGS. 2A and 2B into an elliptical focal spot with a 4:1 axis ratio.

FIG. 5 is a graph schematically illustrating calculated paraxial $1/e^2$ beam-diameter as a function of working distance shift for the inventive objective having the 4:1 specification of TABLE 2, focusing 640 nm, 561 nm, 488 nm, 405 nm, and 355 nm collimated beams from combiner 30 of FIG. 2. The center thicknesses of elements CL1, CL2, and FFL are 4 mm, 2 mm, and 4 mm, respectively. Axial spacing between elements CL1 and CL2 is assumed to be 26.5 mm. Axial spacing between elements CL2 and FFL is assumed to be 1.0 mm.

It can be seen that the horizontal beam waists are significantly tighter than in the 6:1 ratio example of FIG. 3. In the horizontal plane, the working distance shifts for the 355 nm, 405 nm, 488 nm, 561 nm, and 640 nm beams are 0.08 mm, −0.07 mm, −0.07 mm, −0.01 mm, and 0.06 mm, respectively. Accordingly alignment of the horizontal and vertical beam-waists waists is well within a Rayleigh range of the horizontal beam-waists, which, here, is on the order of about 2.0 mm.

While in foregoing examples of the inventive focusing objective the final focusing element FFL has an EFL of 50 mm this should not be considered as limiting. The FFL may have other EFL values without departing from the spirit and scope of the present invention. Examples are presented in TABLE 3 below for a 6:1 ratio of CL1:CL2.

TABLE 3

| Ratio of EFL CL1:CL2 | Optimum EFL of CL1 (mm) | Optimum EFL of CL2 (mm) | EFL of FFL (mm) |
|---|---|---|---|
| 6:1 | 25.25 | −4.21 | 30 |
| 6:1 | 33.92 | −5.65 | 40 |
| 6:1 | 42.30 | −7.05 | 50 |
| 6:1 | 51.71 | −8.62 | 60 |
| 6:1 | 65.64 | −10.94 | 75 |

In the 75 mm EFL example, the working distance shifts for the 355 nm, 405 nm, 488 nm, 561 nm, and 640 nm beams in the horizontal plane are 0.28 mm, −0.23 mm, −0.23 mm, −0.03 mm, and 0.19 mm, respectively. These shifts are comparable with those discussed above for the 50 mm EFL example of TABLE 1 and FIG. 3.

In all examples of the inventive focusing objective described above, all three lens elements are assumed to be fused-silica elements. Comparable optical performance is available, however, if all three elements CL1, CL2, and FFL are made from the same different glass, or if one or more of the elements are made from one glass, and the remaining element or elements are made from another glass.

By way of example TABLE 4 lists a specification of the inventive focusing objective in which all three elements are made from N-BK7 glass. The effective focal lengths of CL1 and CL2 are selected to provide a 6:1 spot-size ratio.

TABLE 4

| Lens (Glass) | EFL (mm) | Center Thickness (mm) | Distance to Previous Lens (mm) |
|---|---|---|---|
| CL1 (N-BK7) | 42.6 | 4 | N/A |
| CL2 (N-BK7) | −7.1 | 2 | 32.9 |
| FFL (N-BK7) | 50 | 4 | 1 |

In the example of TABLE 4, the working distance shifts for the 355 nm, 405 nm, 488 nm, 561 nm, and 640 nm beams in the horizontal plane are 0.27 mm, −0.23 mm, −0.23 mm, −0.03 mm, and 0.19 mm, respectively. These shifts are nearly identical with those discussed above for the 50 mm EFL example of TABLE 1 and FIG. 3.

TABLE 5 lists a specification of the inventive focusing objective in which elements CL1 and CL2 are made from N-BK7 glass, and element FFL is made from fused silica ($SiO_2$). Here again, the effective focal lengths of CL1 and CL2 are selected to provide a 6:1 spot-size ratio.

TABLE 5

| Lens (Glass) | EFL (mm) | Center Thickness (mm) | Distance to Previous Lens (mm) |
|---|---|---|---|
| CL1 (N-BK7) | 45.3 | 4 | N/A |
| CL2 (N-BK7) | −7.55 | 2 | 35.1 |
| FFL (Fused $SiO_2$) | 50 | 4 | 1 |

In the example of TABLE 5, the working distance shifts for the 355 nm, 405 nm, 488 nm, 561 nm, and 640 nm beams in the horizontal plane are 0.063 mm, −0.066 mm, −0.038 mm, −0.010 mm, and 0.027 mm, respectively. These shifts are much less than those discussed above for the 50 mm EFL example of TABLE 1 and FIG. 3.

In all examples of the inventive focusing objective discussed above, the cylindrical lens element CL2 is a negative-power element, i.e., an element having a negative focal length. The inventive objective, however, can be equally effective if element CL2 has a positive optical power in the y-axis, i.e., has a positive focal length.

Figure 6:
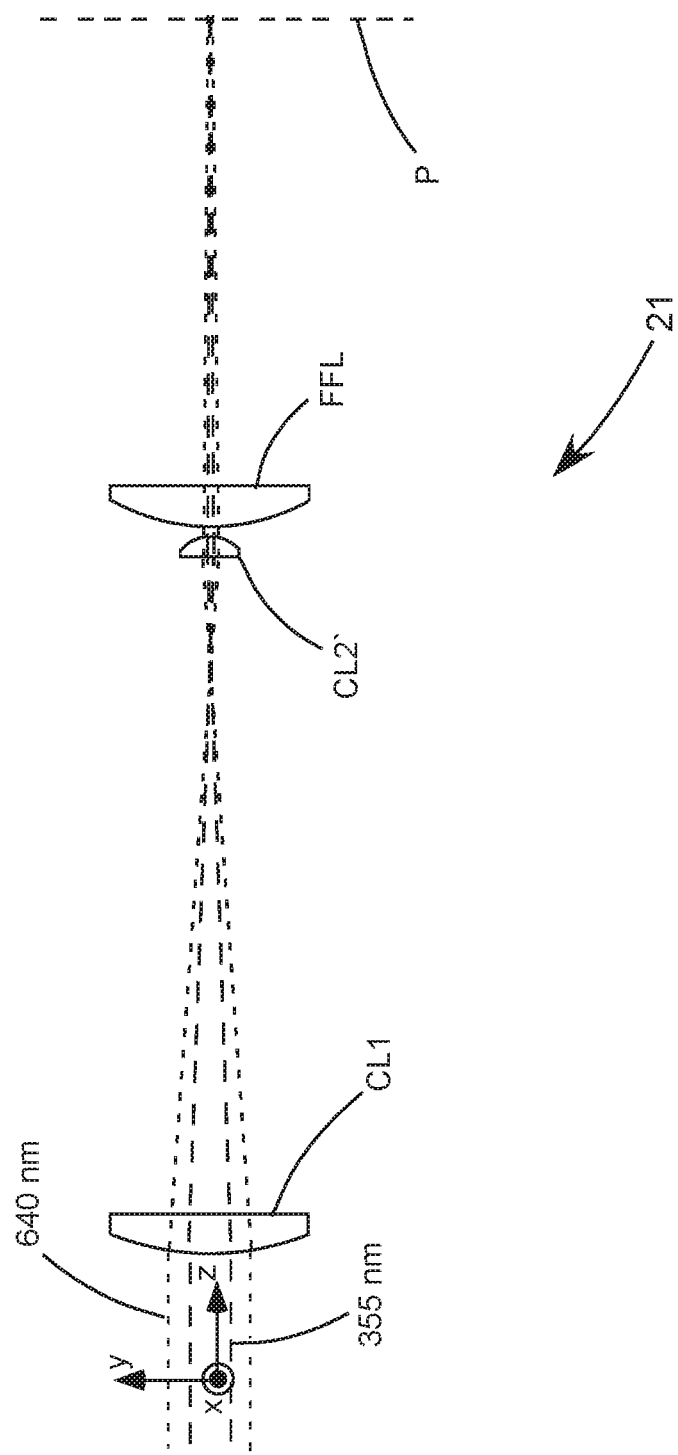
FIG. 6 schematically illustrates another embodiment of the inventive focusing objective, similar to the embodiment of FIGS. 1A and 1B but wherein the negative cylindrical element is replaced by a positive cylindrical lens element.

By way of example, FIG. 6 schematically illustrates an embodiment 21 of the inventive focusing objective in which the second cylindrical element along the z-axis has positive optical power. This element is designated as element CL2' to distinguish the element from element CL2 in FIG. 2 In this drawing, only a horizontal (y-z plane) view is depicted, and only the longest-wavelength (640 nm) and shortest-wavelength (355 nm) input beams are depicted for simplicity of illustration. The 355 nm input beam is preferably smaller than the 640 nm input beam in linear relation to the wavelength, as discussed above. Input beams are focused into a working plane P.

An exemplary specification for objective 21 is provided in TABLE 6. All three lens elements are assumed to made form fused-silica. EFLs of CL1 and CL2' are selected to provide a 6:1 spot-size ratio.

TABLE 6

| Lens | EFL (mm) | Center Thickness (mm) | Distance to Previous Lens (mm) |
|---|---|---|---|
| CL1 | 59.2 | 4 | N/A |
| CL2' | 9.9 | 2 | 65 |
| FFL | 50 | 4 | 1 |

In the example of TABLE 6, the working distance shifts for the 355 nm, 405 nm, 488 nm, 561 nm, and 640 nm beams in the horizontal plane are 0.57 mm, −0.52 mm, −0.50 mm, −0.07 mm, and 0.43 mm, respectively. These shifts are comparable with those discussed above for the 50 mm EFL example of TABLE 1 and FIG. 3. It can be seen however that the length of the objective is increased by a need for an extended spacing between CL1 and CL2' to accommodate the positive focal length of CL2'.

In all of the examples of the inventive focusing objective described above all of the lens elements are either plano-convex or plano-concave. This is particularly advantageous in minimizing production costs for the elements. As the design does not require any cemented elements the objective can be used to focus ultraviolet radiation without any degradation of lens elements. Further, the number of available focal length selection options offers a possibility that one or more of the lens elements could be an "off the shelf" lens element from a catalog optics supplier. This is particularly true of the spherical element FFL.

It should be noted that the exemplary wavelengths for radiations being focused used throughout the above presented should not be considered as limiting. Those skilled will recognize from the description that the objective can be designed to focus other wavelengths without departing from the spirit and scope of the present invention.

In summary, the present invention is described above with reference to preferred embodiments and examples thereof. The invention, however, is not limited to the embodiments and examples described and depicted herein, rather the invention is limited only by the claims appended hereto.

What is claimed is:

1. Optical apparatus comprising
at least first, second, third, and fourth lasers delivering respectively first, second, third, and fourth component laser-beams at respectively first, second, third, and fourth wavelengths;
a beam combiner arranged to combine the first, second, third, and fourth component laser-beams into a combined beam; and
an objective lens including only three singlet optical elements arranged to receive the combined laser-beam and focus the combined laser-beam such that the component laser-beams thereof are all focused about in a common focal plane, wherein the three singlet optical elements are first, second, and third single optical elements arranged in sequential order along the propagation direction of the combined laser beam, said first and second singlet optical elements are cylindrical elements and the third singlet optical element is a spherical element.

2. Optical apparatus comprising
at least first, second, third, and fourth lasers delivering respectively first, second, third, and fourth component laser-beams at respectively first, second, third, and fourth wavelengths, wherein the first second third and fourth wavelengths are respectively about 405 nm, about 488, about 561 nm, and about 637 nm;
a beam combiner arranged to combine the first, second, third, and fourth component laser-beams into a combined beam; and
an objective lens including only three singlet optical elements arranged to receive the combined laser-beam and focus the combined laser-beam such that the component laser-beams thereof are all focused about in a common focal plane.

3. Optical apparatus comprising
at least first, second, third, and fourth lasers delivering respectively first, second, third, and fourth component laser-beams at respectively first, second, third, and fourth wavelengths, with the wavelengths decreasing in numerical order of recitation;
first, second, third, and fourth telescopes arranged to expand the component laser beams into respectively first, second, third, and fourth collimated component laser beams having respectively first, second, third, and fourth beam diameters with the beam diameters decreasing in numerical order of recitation;
a beam combiner arranged to combine the first, second, third, and fourth collimated component laser-beams into a combined beam; and
an objective lens including only three singlet optical elements arranged to receive the combined laser-beam and focus the combined laser-beam such that the component laser-beams thereof are all focused about in a common focal plane.

4. The apparatus of claim 3, wherein the first, second, third, and fourth beam diameters decrease in about a linear relationship with the respective wavelengths.

5. The apparatus of claim 3, wherein the three singlet optical elements consist of a first cylindrical element having a focal length $f_{CL1}$, second cylindrical element having a focal length $f_{CL2}$, and a spherical element having a focal length $f_{FFL}$ arranged sequentially in a direction of propagation of the combined beam, and
wherein $f_{CL1}$, $f_{CL2}$, and $f_{FFL}$ are related by an equation $$f_{CL1} - f_{CL2} = G * f_{FFL}$$

where G is between about 0.7 and about 1.4.

6. The apparatus of claim 5, wherein G is between about 0.9 and about 1.1.

7. The apparatus of claim 5, further including a fifth laser delivering a fifth component laser beam having a wavelength less than that of the fourth component laser beam, a fifth telescope expand the fifth component laser beams into a collimated component laser beam having a fifth diameter less than the fourth diameter, and wherein the beam combiner is arranged to combine all five collimated component beams into the combined beam.

* * * * *